(12) United States Patent
Cohen et al.

(10) Patent No.: US 8,187,626 B2
(45) Date of Patent: May 29, 2012

(54) WOUND DRESSINGS CONTAINING COMPLEXES OF TRANSITION METALS AND ALGINATE FOR ELASTASE-SEQUESTERING

(75) Inventors: Kelman I. Cohen, Richmond, VA (US); Yousef Mohajer, Midlothian, VA (US)

(73) Assignee: Tissue Technologies, LLC, Richmond, VA (US)

( * ) Notice: Subject to any disclaimer, the term of this patent is extended or adjusted under 35 U.S.C. 154(b) by 0 days.

(21) Appl. No.: 12/779,108

(22) Filed: May 13, 2010

(65) Prior Publication Data

US 2010/0221311 A1 Sep. 2, 2010

Related U.S. Application Data

(63) Continuation-in-part of application No. 10/446,806, filed on May 29, 2003, now abandoned, which is a continuation-in-part of application No. 09/515,172, filed on Feb. 29, 2000, now Pat. No. 6,627,785.

(51) Int. Cl.
 *A61F 13/00* (2006.01)
(52) U.S. Cl. .......................................... 424/443
(58) Field of Classification Search ................... 424/443
 See application file for complete search history.

(56) References Cited

U.S. PATENT DOCUMENTS

| | | | |
|---|---|---|---|
| 3,238,100 A * | 3/1966 | Meyer et al. ................ | 424/601 |
| 4,391,799 A | 7/1983 | Mason, Jr. et al. | |
| 4,453,939 A | 6/1984 | Zimmerman et al. | |
| 5,098,417 A | 3/1992 | Yamazaki et al. | |
| 5,470,576 A | 11/1995 | Patel | |
| 5,688,522 A | 11/1997 | Hardy | |
| 5,688,923 A | 11/1997 | Gerrish et al. | |
| 5,696,101 A | 12/1997 | Wu et al. | |
| 5,718,916 A | 2/1998 | Scherr | |
| 5,735,812 A | 4/1998 | Hardy | |
| 5,807,555 A | 9/1998 | Bonte et al. | |
| 5,836,970 A | 11/1998 | Pandit | |
| 5,888,987 A | 3/1999 | Haynes | |
| 5,897,590 A | 4/1999 | Donovan | |
| 5,925,009 A | 7/1999 | Mahoney et al. | |
| 5,998,692 A | 12/1999 | Gilding | |
| 6,015,816 A | 1/2000 | Kostyniak | |
| 6,022,556 A | 2/2000 | Hardy | |
| 6,153,214 A | 11/2000 | Horsler | |
| 6,333,093 B1 | 12/2001 | Burrell et al. | |
| 6,348,423 B1 | 2/2002 | Griffiths et al. | |

(Continued)

FOREIGN PATENT DOCUMENTS

GB 2 221 620 2/1990

(Continued)

OTHER PUBLICATIONS

International Search Report dated Jun. 17, 2008.

(Continued)

*Primary Examiner* — Isis Ghali
(74) *Attorney, Agent, or Firm* — Whitham Curtis Christofferson & Cook, PC (57) ABSTRACT

Transition metal (e.g., silver and copper) derivatized phosphorylated polysaccharides (cellulose, starch, gauze) provide antimicrobial and elastase sequestration properties to wound dressings, and the wound dressing have enhanced water sorption and elastase sequestration when used with alginates. Wound dressings with alginates (e.g., silver alginate, crosslinked alginates, etc.) provide enhanced wound fluid absorption as well as elastase sequestration.

2 Claims, 4 Drawing Sheets

U.S. PATENT DOCUMENTS

| | | |
|---|---|---|
| 6,440,940 B1 | 8/2002 | Doyle et al. |
| 6,566,576 B1 | 5/2003 | Komerska et al. |
| 6,599,523 B2 | 7/2003 | Cohen et al. |
| 6,627,785 B1 | 9/2003 | Edwards et al. |
| 6,656,974 B1 | 12/2003 | Renn et al. |
| 6,696,077 B2 | 2/2004 | Scherr |
| 6,809,231 B2 | 10/2004 | Edwards |
| 6,861,570 B1 | 3/2005 | Flick |
| 6,911,437 B2 | 6/2005 | Edwards et al. |
| 6,956,144 B2 | 10/2005 | Molan |
| 7,005,556 B1 | 2/2006 | Becker |
| 7,101,862 B2 | 9/2006 | Cochrum et al. |
| 7,112,320 B1 | 9/2006 | Beaulieu et al. |
| 7,128,929 B1 | 10/2006 | Scherr |
| 7,214,847 B1 | 5/2007 | Flick |
| 7,230,153 B2 | 6/2007 | Flick |
| 7,291,762 B2 | 11/2007 | Flick |
| 7,910,130 B2 | 3/2011 | Mohajer et al. |
| 2004/0010900 A1 | 1/2004 | Horn et al. |
| 2004/0241213 A1 | 12/2004 | Bray |
| 2005/0101900 A1 | 5/2005 | Qin et al. |
| 2005/0147657 A1 | 7/2005 | Canada et al. |
| 2006/0142242 A1 | 6/2006 | Mohajer et al. |
| 2008/0305138 A1 | 12/2008 | Cullen et al. |
| 2009/0035342 A1 | 2/2009 | Karandikar et al. |

FOREIGN PATENT DOCUMENTS

| | | |
|---|---|---|
| JP | 9-256226 | 9/1997 |
| WO | WO98/00180 | 1/1998 |

OTHER PUBLICATIONS

All Med Wholesale, downloaded Feb. 7, 2012, 3 pages.

* cited by examiner

Figure 4F

WOUND DRESSINGS CONTAINING COMPLEXES OF TRANSITION METALS AND ALGINATE FOR ELASTASE-SEQUESTERING

CROSS REFERENCE TO RELATED APPLICATIONS

This is a continuation-in-part of application Ser. No. 10/446,806 filed May 29, 2003, now abandoned which is a continuation-in-part of U.S. patent application Ser. No. 09/515,172, entitled "Wound Dressing with Protease-Lowering Activity," filed on Feb. 29, 2000, now U.S. Pat. No. 6,627,785, that are incorporated herein in entirety by reference.

FIELD OF THE INVENTION

The invention generally relates to wound dressings and their methods of use. In particular, the invention provides wound dressings with associated active agents such as protease inhibitors and sequestrants which enhance the healing of wounds, especially chronic wounds.

BACKGROUND OF THE INVENTION

The normal response to tissue injury is a timely and orderly reparative process that results in sustained restoration of anatomic and functional integrity.(Lazarus, et al. 1994). In contrast, in chronic ulcers, the healing process is prolonged, incomplete and proceeds in an uncoordinated manner resulting in poor anatomical and functional outcome. Clinically, wounds are categorized as acute and chronic based on the timeliness of healing.

Most chronic ulcers are associated with a small number of well-defined clinical entities particularly chronic venous stasis, diabetes mellitus, and pressure ulcers. These conditions are responsible collectively for approximately 70% of all chronic ulcers (Nwomeh et al. 1998). The incidence and prevalence of chronic ulcers vary considerably but are especially high in spinal cord injury patients as well as the elderly and nursing home population. As our society continues to age it is predicted that the incidence of chronic ulcers will continue to increase dramatically. Patients with pressure ulcers also have a significant socioeconomic impact on our society. For example, health care expenditures for treating pressure ulcers alone have been estimated to exceed $3 billion a year (Nwomeh, et al. 1998). Normal healing involves a complex cascade of events involving interaction among many cell types, soluble factors and matrix components. Healing can be arbitrarily divided into overlapping temporal phases of coagulation, inflammation fibroplasia and finally remodeling. Most of the events are cytokine regulated. Normally, during the inflammatory phase, polymorphonuclear leukocytes (PMNs) are the first of the leukocytes to appear. They produce various proteases such as MMP-8 (collagenase) and elastase, which help to remove damaged matrix and aid in healing. In both the open acute and chronic wound, various cytokines are important in contraction and spontaneous closure of the wound as well as angiogenesis. Under normal circumstances, closure of the open wound is aided further by epithelization as these surface cells seal the final closure.

Chronic wounds are very different. For example, pressure ulcers are characterized by deep tissue necrosis with loss of muscle and fat that is disproportionally greater then the loss of overlying skin (Falanga, et al. 1998). These defects are common among the immobilized and debilitated. There are approximately 225,000 spinal cord injury patients in the United States and approximately 9,000 new cases per year. Approximately 60% of these patients develop pressure ulcers and the annual cost is greater then $25,000 per patient for medically related care.(Allman, 1998) If the elderly nursing home population with pressure ulcers in added to the spinal cord injury population then the figure for the care of all pressure ulcers is enormous.

To date, the majority of the effort to improve rates of healing of chronic wounds have focused on the use of exogenous peptide growth factors and cell based products such as cytokines. For the most part, these attempts have met with little notable success. Another alternative approach has been the use of "skin substitutes" such as Apligraf (matrix+cells) and Dermagraft (matrix+cells). While this second approach has shown some promise, its expense presently greatly limits its use to the richer developed countries. Various modifications of the wound dressings have also been suggested as a meant to augment would healing.

Further examples include:

U.S. Pat. No. 5,098,417 to Yamazaki et al. teaches the ionic bonding of physiologically active agents to cellulosic wound dressings.

U.S. Pat. No. 4,453,939 to Zimmerman et al. teaches the inclusion of aprotonin in composition for "sealing and healing" of wounds. U.S. Pat. No. 5,807,555 to Bonte et al. teaches the inclusion of inhibition for alpha-1-protease, collagenase, and elastase in pharmaceutical compositions for promotion of collagen synthesis.

U.S. Pat. No. 5,696,101 to Wu et al., teaches use of oxidized cellulose (e.g. Oxycel) as a bactericide and hemostat in treatment of wounds.

World Patent WO 98/00180 to Watt et al. teaches complexation of oxidized cellulose with structural proteins (e.g. collagen) for chronic wound healing; and references the utility of oligosaccharide fragments produced by the breakdown of oxidized cellulose in vivo in the promotion of wound healing.

Neutrophils are a predominant infiltrating inflammatory cell type present in the acute inflammatory response. Neutrophils function primarily to destroy invading pathogens and to debride devitalized tissue at the site of injury. The normal adult produces approximately $10^{11}$ neutrophils per day. To function effectively in host defense, they must migrate to the site of inflammation and release selectively a large repertoire of lytic enzymes, antimicrobial peptides, and potent oxidants from cytoplasmic granules. Under other conditions, the neutrophil has been implicated in causing disease by damaging normal host tissue. Such inflammatory tissue injury are important in the pathogenesis of a variety of clinical disorders including arthritis, ischemia-reperfusion tissue injury and systemic inflammatory response syndrome (SIRS) and the acute respiratory distress syndrome(ARDS).(Weiss, 1989) There is strong evidence that neutrophils also may have a significant role in the pathophysiology of pressure ulcers.

Neutrophils are a prevalent cell type in pressure ulcers. (Diegelmann, et al. 1999; Paloahti. et al. 1993; Rogers et al. 1995) In addition, there is direct evidence correlating neutrophil products with chronic pressure ulcers.(Yager, et al. 1996; Yager, et al. 1997). This includes neutrophil elastase, gelatinase (MMP-9) as well as collagenase (MMP-8).(Wysocki, 1996; Wysocki et al, 1993; Yager et al. 1997; Yager et al. 1996). Therefore, these observations and the evidence that neutrophils have been implicated in tissue destruction in other inflammatory processes give strong credence to the hypothesis that neutrophil products are involved in the pathogenesis of pressure sores and subsequent failure to heal. Neutrophil-derived MMP-8 has been shown to be the predominant collagenase in both acute and chronic wounds.(Nwomeh, et al. 1999).

Neutrophils contain large amounts of elastase (1 pg/cell). This serine protease has a broad substrate spectrum. As with neutrophil-derived MM-8, elastase levels have also been found to be significantly elevated in fluid derived from pressure ulcers.(Yager et al: 1997) The presence of high levels of active elastase with a wound site may have important implications for wound healing therapies utilizing peptide growth factors. Elastase present in chronic wounds can degrade peptide growth factors such as PDGF and TGF-b.(Yager et al. 1997). Moreover, cell surface receptors for peptide growth factors may themselves be functionally inactivated by the actions of elastase. Elastase may also contribute to the overall proteolytic environment of chronic wounds. It is known to proteolytically inactivate the specific inhibitor, Tissue Inhibitor of Metalloproteinases (TIMP). In addition, elastase itself may participate in proteolytically activating collagenase and gelatinase zymogens. Obviously, an unregulated proteolytic environment can be a significant aspect of the pathophysiology of chronic wounds.

It would be highly beneficial to have available additional methods for enhancing wound healing. In particular, methods directed to bringing the proteolytic environment of wounds under control in order to promote wound repair would be desirable. Such methods would be useful in the treatment of wounds in general, and chronic wounds in particular. Further, it would be highly beneficial if such methods were inexpensive and thus widely accessible.

A number of patents and patent applications describe the use of alginates in the treatment of burns or wounds. For example, U.S. Pat. No. 6,696,077 to Scherr describes various silver alginate foam compositions, and U.S. Pat. No. 6,809,231 to Edwards describes cross-linked alginate formulations.

A number of patents and patent applications describe the use of silver ions as antimicrobial agents. For example, U.S. Patent Publication 2005/010900 to Qin describes polysaccharide fibers, formed with alginate that contain a silver compound as an antimicrobial agent, and U.S. Patent Publication 2004/0241213 to Bray describes carboxymethyl cellulose or alginate fibers in a mixture that contains silver ions. Neither reference describes a configuration where alginates are position in a wound dressing for sequestration of elastase.

SUMMARY OF THE INVENTION

It is an object of this invention to provide novel wound dressings for the treatment of wounds, especially for the treatment of chronic, non-healing wounds. The wound dressings of the instant invention are comprised of a support matrix which is preferably cellulose, carboxymethylated cellulose, dialdehyde gauze, sulfonated gauze, and phosphorylated gauze, in combination with silver or copper, alginate or silver alginate. The wound dressings combine antimicrobial activity together with elastase sequestration and provide for enhanced wound healing in burns, surgical wounds, ulcers and chronic wounds, etc. For example, in some embodiments, the gauze may be derivatives with silver and then coated with alginate. In other cases, the gauze may be coated with silver alginate which may be bound to the support matrix or be able to dissociate from the support matrix so as to allow migration in the wound microenvironment. When phosphorylated gauze, sulfonated gauze or dialdehyde gauze is used as a support matrix, the wound dressing benefits from elastaste sequestration by the gauze itself as well as by the alginate. The sequestrants bind proteases found in the wound fluid and remove them from the wound microenvironment.

The invention also provides-methods of use for the wound dressings, including a method for sequestering elastase at a wound site. This method comprises the step of contacting the wound site with a wound dressing selected form the group consisting of carboxymethylcellulose, dialdehyde gauze, sulfonated gauze, and phosphorylated gauze together with transition metal such as silver and alginate.

The dressings may be applied to wounds in order to enhance would healing, especially the healing of chronic wounds.

DETAILED DESCRIPTION OF THE PREFERRED EMBODIMENTS OF THE INVENTION

The present invention is based upon the previously unrecognized discovery that active agents such as inhibitors and sequestrants of proteases may be used as healing accelerants of wounds, and of chronic wounds in particular. These inhibitors and sequestrants may be physically applied on wound dressings, or in the alternative may be ionically or covalently conjugated to a wound dressing material for purposes of sustained release of active agent or sequestration of endogenous constituents from the wound environment. In a preferred embodiment of the present invention, the active agents inhibit or bind cationic, neutrophil-derived proteases such as neutrophil elastase.

Specific pharmacological effects of proteases inhibitors and sequences associated with wound dressings include inhibition of the breakdown of growth factors that stimulate migration of cells to the ulcer site of the wound, leading to the growth of new tissue that heals the open wound. This technology is broadly applicable to all forms of chronic wounds including diabetic ulcers and decubitus bedsores. Both peripheral and central administration of the compounds formulated on wound dressings accelerate wound healing of chronic wounds. Silver complexed to matrix and silver alginate are shown herein to have potent elastase sequestering properties which were heretofore previously unrecognized and thereby inhibit proteases such as human elastase and thus prevent growth factor and tissue degradation. Alternatively, the silver alginate may be bound (chemically (ionic or covalently) or physically) to the wound dressing. As a component of such a matrix, they are able to sequester destructive proteases from the microenvironment of the wound, thus preventing the degradation of growth factors and fibronectin that would otherwise occur.

The therapeutic administration of the modified wound dressings containing inhibitors include a pharmacologically effective dose of the inhibitor or sequestrant (e.g., silver alginate, or silver alginate in combination with a phosphorylated, sulfonated or dialdehyde gauze) when used in the treatment of a patient in need thereof. The dose of inhibitor or sequestrant required on the wound dressing to promote accelerated healing in the patient ranges from about 0.2 mg/gram fiber to about 200 mg/gram fiber per day, with this in turn being dependent upon specific factors including patient health, wound type, etc. The term "patient" used herein is taken to mean mammals such as sheep, horses, cattle, pigs, dogs, cats, rats, mice and primates, including humans.

The term "wound dressing" used herein is taken to include any pharmaceutically acceptable wound covering or support matrix such as:

a) films, including those of a semipermeable or a semi-occlusive nature such as polyurethane copolymers, acrylamides, acrylates, paraffin, polysaccharides, cellophane and lanolin.

b) hydrocolloids including carboxymethylcellulose protein constituents of gelatin, pectin, and complex polysaccharides including Acacia gum, guar gum and karaya. These materials may be utilized in the form of a flexible foam or, in the alternative, formulated in polyurethane or, in a further alternative, formulated as an adhesive mass such as polyisobutylene.

c) hydrogens such as agar, starch or propylene glycol; which typically contain about 80% to about 90% water and are conventionally formulated as sheets, powders, pastes and gels in conjunction with cross-linked polymers such as polyethylene oxide, polyvinyl pyrollidone, acrylamide, propylene glycol.

d) foams such as polysaccharide which consist of a hydrophilic open-celled contact surface and hydrophobic closed-cell polyurethane.

e) impregnates including pine mesh gauze, paraffin and lanolin-coated gauze, polyethylene glycol-coated gauze, knitted viscose, rayon, and polyester.

f) cellulose-like polysaccharide such as alginates, including calcium alginate, which may be formulated as non-woven composites of fibers or spun into woven composites.

Preferred wound dressings are polysaccharide containing support matrices which are derivatized with silver or copper and/or which have silver alginate bound to or placed upon them, and it is envisioned to include chitosans, alginates (e.g., cross-linked or in a form other than silver alginate) and cotton or carboxymethylated cotton in the form of gauze, films, hydrocolloide, hydrogels, hydroactives, foams, impregnates, absorptive powders and pastes, Especially preferred wound dressings include cotton cellulose formed as woven or non-woven gauze. This type of wound dressing has the advantage of being readily available and relatively inexpensive. In this case, the protease sequestrant or inhibitor may be linked to the cellulose polysaccharide chain through a chemical substituent such as amino, carboxylate, citrate, phosphate, sulfonate, chloride, bromide, mono-carboxylic acid, di-carboxylic acid, tri-carboxylic acid; or, any pharmaceutically acceptable salt thereof. Exemplary salts are seen to include those of acids such as acetic, glycolic, lactic, pyruvic, malonic, succinic, glutaric, fumaric, malic, tartaric, ascorbic, maleic, hydroxymaleic, benzoic, hydroxybenzoic, phenylacetic, cinnamic, salicylic, and 2-phenoxyhenzoic; and sulfonic acids such as methane sulfonic acid and hydroxyethane sulfonic acid. Salts of the carboxy terminal amino acid moiety may include the nontoxic carboxylic acid salts formed with any suitable inorganic or organic bases. illustratively, these salts include those of alkali metals, as for example, sodium and potassium; alkaline earth metals, such as calcium and magnesium; light metals of Group IIA elements including aluminum, and organic primary, secondary, and tertiary amines, as for example, trialkylamines, including triethylamine, procaine, dibenzylamine, 1-ethenamine, N,N'-dibenzylethylenediamine, dihydroabietylamine, N-alkylpiperidine and any other suitable amine.

The wound dressings of the instant invention may be used alone or as an adjunct to other therapeutic measures. For example, the wound dressings may be used together with the administration of exogenous growth factors. Obviously, conditions that increase the stability of an exogenous peptide growth factor or its receptor will likely promote its efficacy. The wound dressings of the present invention may also be used in conjunction with skin grafts, in which case a proteolytic environment that is under control will less likely cause the "rejection" or melting of a skin substitute graft.

The wound dressings may also include other therapeutically beneficial substances such as antibiotics, vitamins, and the like.

The dressings and methods of the present invention may be utilized to treat any type of appropriate wound. In a preferred embodiment, the wound that is treated is a chronic, non-healing wound.

The invention is illustrated by the following Examples which are intended to be illustrative but should in no way be construed as limiting.

EXAMPLES

Carboxymethylated and Dialdehyde Cotton Gauze

Methods

Preparation of Dialdehyde Cotton Gauze

Dialdehyde cotton gauze (also referred to as 2,3 dialdehyde-anhydroglucos-cellulose, oxidized cellulose, oxycellulose, or periodate-oxidized cellulose) was prepared as follows: cotton gauze (12 ply-4 in.×4 in.), USP type VII, were treated under three different reaction conditions in lots of 50 gauze sponges as follows: Treatment 1: a 0.07 M solution of sodium periodate for 1 h at 45° C. with a solution pH of 4.2. Treatment 2: a 0.2 M solution of sodium periodate for 1.5 h at 45° C. with a solution pH of 4.5. Treatment 3: a 0.2 M solution of sodium periodate for 3 h at 45° C. with a solution pH of 4.5. Following the treatment excess periodate was removed by rinsing the gauze through a screen under running tap water. Following the rinse cycle the gauze samples were passed through a conventional ringer to remove excess moisture. The samples were then separated and placed on a wire rack to air dry overnight. The dried gauzes were placed in Chex all II™ instant sealing pouches (5 in.×10 in.) and sterilized with ethylene oxide gas by Micro Test Laboratories, Agauam, Mass.

Preparation of Carboxymethylated Cotton Gauze

Carboxymethylation was completed as outlined previously (Liyanage et al, 1995). A solution was made by mixing 24 parts of dichloroacetic acid with 24 parts of water, and while cooling in an ice bath, stirring in 75 parts of sodium hydroxide solution. This solution was used to pad a sample of cotton gauze to a wet pickup of 135%. The wet sample was then placed in an oven at 100° C. and dried/cured for 10 minutes.

Determination of Dialdehyde Content and Degree of Substitution of Carboxymethylcellulose Previously outlined procedures were employed to determine the dialdehyde content (Hofreiter et al. 1995) and the degree of substitution for the carboxymethylated gauze (Reinhardt et al.)

Assay of Treated Gauze for Elastase Activity

Treated and untreated gauze samples were submerged in 1 milliliter of buffer containing 0.1 units/ml of human neutrophil elastase. The samples were allowed to incubate for one hour at room temperature, and the gauze samples were removed and placed in a press to drain unbound buffer and enzyme. The unbound buffer and enzyme fractions were combined and assayed for elastase activity as described below.

Enzyme Assays

Enzyme assays of the solutions containing unbound human neutrophil elastase were conducted in pH 7.6 buffer composed of 0.1 M sodium phosphate, 0.5 M NaCl, and 3.3% DMSO and subjected to spectrophotometric measurement of the release of p-nitroaniline at 410 nm from the enzymatic hydrolysis of MeOSuc-Ala-Ala-Pro-Val-pNA (Sigma). The spectrophotometric kinetic assays were performed in a Bio-Rad Microplate Reader (Hercules, Calif.) with a 96-well format. 200 microliter aliquots of a elatase solution (0.2 units) were assayed to initiate the enzyme reaction.

Results

The gauze finishes employed in this study were prepared to assess the effect of 1) both sterilization and variation of the sodium periodate finishing conditions on the activity of dialdehyde cotton gauze in reducing elastase activity; and 2) the effect of the degree of substitution of carboxymethylated gauze in reducing elastase activity.

Figure 1A:
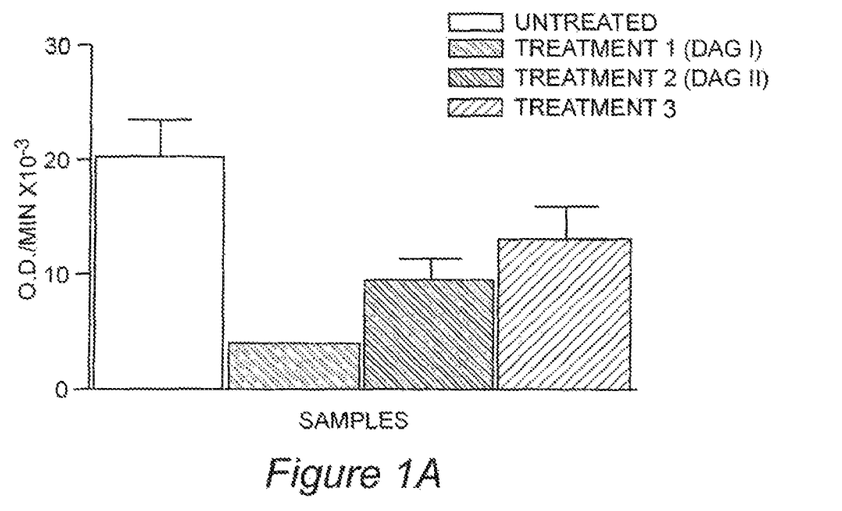
FIGS. 1A and 1B. Assessment of reduction in human neutrophil elastase activity in samples of HLE after exposure to modified cotton gauze. 3A: FILE samples were exposed to three different oxidized cotton gauze samples corresponding to gauze Treatment Methods 1, 2 and 3 (see Methods, Preparation of Dialdehyde Cotton Gauze). 3B: HLE samples were exposed to 25 and 50 mg of two different carboxymethylated cotton gauze samples, III and IV (see Methods, Preparation of Carboxymethylated Cotton Gauze). Untreated gauze was employed as a control. Data are mean±S.D. of triplicate determinations.

As shown in FIG. 1A, variation of the oxidation conditions, and hence percent aldehyde incorporation, effects elastase-lowering activity of the dialdehyde cotton gauze. The results of these studies suggests that Treatment #1 is optimal for retaining efficacy of the dialdehyde cotton gauze. Prolonged exposure and higher periodate concentration, which is correlated with fewer dicarbonyl units in the cotton cellulose, appears to decrease the efficacy of the gauze in reducing elastase activity in solution.

Figure 1B:
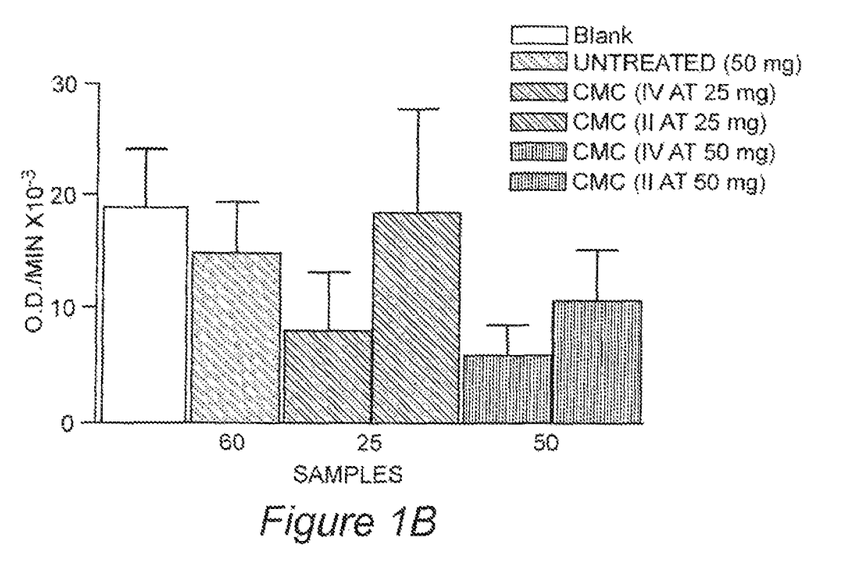

Two different degree of substitution (DS) levels of carboxymethylated cotton cellulose were also compared. As shown in FIG. 1B, higher substitution levels of carboxylate on cotton resulted in an increased reduction in elastase activity in solution.

Correlation of decreased enzyme activity with number of carboxylate or aldehyde sites on cellulose observed within a narrow range of enzyme rates of activity suggests that the cotton derivatized aldehyde and carboxylates bind elastase into readily accessible binding sites in the modified cotton fiber of the gauze.

These results suggest that dialdehyde cotton gauze and carboxymethylated gauze can be used to effect the sequestration of the protease elastase from solutions of the enzyme.

Oxidized, Sulfonated, and Phosphorylated Cotton Gauze Dressings Selectively Absorb Neutrophil Elasase Activity in Solution Methods Preparation of Periodate-Oxidized, Sulfonated, and Phosphorylated Cotton 2,3 dialdehyde-anhydroglucose-cellulose (i.e. periodate oxidized) cotton. Cotton gauze (12 ply-4 in.×4 in.), USP type VII, was treated in lots of 50 gauze sponges in a 0.07 M solution of sodium periodate for 1 h at 45° C. with a solution pH of 4.2. Alternatively, cotton gauze was oxidized with 0.2M sodium metaperiodate (pH 5) at 40° C. for 3 hours. Following the treatment excess periodate was removed by rinsing the gauze through a screen under running tap water. Following the rinse cycle, the gauze were passed through a conventional ringer to remove excess moisture. The samples were then separated and placed on a wire rack to air dry overnight. The dried gauze are placed in a Chex all II™ instant sealing pouch (5×10 in.) and sterilized with ethylene oxide gas by Micro Test Laboratories, Agauam, Mass.

Sulfonated cotton. The cotton gauze may be sulfonated by washing the dialdehyde oxycellulose with 5% sodium bisulfite ($NaHSO_3$) under pH 4.5, liquor ratio 1:60 for 3 hours. Excess sodium bisulfite may be removed by rinsing with water under running tap water. Following the rinse cycle the gauze are passed through a conventional ringer to remove excess moisture. The samples are then separated and placed on a wire rack to air dry overnight.

Phosphorylated cotton. Phosphorylation of cotton gauze is accomplished by applying inorganic phosphate salt (sodium hexametaphosphate) to cotton gauze in 4-16% composition. Urea is usually included in the formulation on a 2:1 weight ratio of urea to phosphate. All formulations contained 0.1% Triton X-100 as a wetting agent. The cotton gauze is padded to 80-90% wet pickup and then dried at 60° C. The samples are cured at 160° C. for 7 min.

The phosphorylated and sulfonated cotton cellulose D.S. levels were 0.035 and 0.011 respectively, as measured by elemental analysis.

Carboxymethylated Cotton Gauze

Carboxymethylation was completed as outlined previously (Reinhart et al. 1957). A solution was made by mixing 24 parts of dichloroacetic acid with 24 parts of water and while cooling in an ice bath stirring in 75 parts of sodium hydroxide solution. This solution was used to pad a sample of cotton gauze to a wet pickup of 135%. The wet sample was then placed in an oven at 100° C., and dried/cured for 10 minutes.

Free-Swell Absorbency and Wicking Test

A free-swell absorbency test was performed as follows: A 0.5 gram sample of the cotton gauze was placed in 30 mL of a 0.9% by weight aqueous saline solution and left for 5 minutes. The cotton textile was then filtered through a sintered Mark 1 funnel of pore size 100-160 microns and is left for 5 minutes, or until it stops dripping. The water filtered through the funnel was weighed and the weight of water absorbed by the filaments is calculated by subtraction. A wicking test was made by immersing the cotton gauze in deionized water containing foxboro red dye such that the gauze was just touching the water surface. The time required for the dye solution to migrate 1.5 cm on the gauze strip was measured.

Patients and Wound Fluid

Informed consent was obtained for all procedures, and approval was received from the Virginia Commonwealth University Committee on the Conduct of Human Research, in accordance with the 1975 Declaration of Helsinki. Fluids were harvested from a grade III trochanteric pressure ulcer of a patient with spinal cord injury using a sub-atmospheric device (V.A.C.®,KCI, San Antonio, Tex.). Fluids were clarified by centrifugation at 14,000 g for 15 min at 4° C. The protein concentration was determined with the Bio-Rad Protein assay (Richmond, Calif.) with bovine serum albumin as a quantitation standard.

Assay of Wound Fluid

The patient wound fluid was diluted (1:100; wound fluid: buffer; v:v) at a volume of 3 mL with buffer (0.1M sodium phosphate, 0.5 M NaCl, and 3.3% DMSO) and incubated with weighed samples of gauze ranging from 75 mg to 700 mg. The gauze samples were soaked in the wound fluid solutions for one hour whereupon the solutions were filtered from the gauze under pressure applied to the gauss using a Whatman Autovial (0.45 micron PFTE membrane). Recovery of the wound fluid solution from the gauze was judged to be 90%. The wound fluid solution was assayed for elastase activity in a manner similar to the elastase enzyme assay described below. Rates of substrate hydrolysis were measured on a reaction progress curve of absorbance versus time.

Sequestration and Inhibition of Elastase Activity by Finished Cotton Gauze

The effect of a variety of cotton gauze finishes was tested to assess extraction of elastase from solution. Carboxymethylated, sulfonated, phosphorylated, and oxidized cotton gauze were assayed as 50 and 75 milligram samples of type VII cotton gauze (used typically in patients with chronic wounds). Treated and untreated gauze samples were submerged in 1 milliliter of buffer containing 1 unit/mL of human neutrophil elastase. The samples were allowed to incubate for one hour at room temperature, and each individual gauze sample was removed and placed in an Autovial press filter (Whatman,) to extract unbound buffer and enzyme. The filtered fraction of each individual sample was re-combined with solution not taken up by the gauze and assayed for elastase activity.

The modified gauze containing bound elastase was assessed for recoverable enzyme activity by pooling gauze samples and extracting bound elastase with 20% acetic acid solution. Samples of 1-2 grams of modified gauze were soaked in acetic acid solutions, filtered and the solutions lyophilized to dryness. The lyophilized pellet was resuspended in buffer, filtered on a sintered glass filter funnel and the resulting solution was assayed in 200 microliter aliquots. Elastase activities recovered from the gauze were 43 milliunits per gram in untreated gauze and 160 milliunits per gram from dialdehyde cotton gauze.

Enzyme Assays

Enzyme assays of the solutions containing unbound human neutrophil elastase were conducted in pH 7.6 buffer composed of 0.1M sodium phosphate, 0.5 M NaCl, and 3.3% DMSO and subjected to spectrophotomeric measurement of the release of p-nitroaniline at 410 nm from the enzymatic hydrolysis of N-Methoxysuccinyl-Ala-Ala-Pro-Val-p-nitoranilide (Sigma) (Nakajima et al. 1979). The spectrophotometric kinetic assays were performed in a Bio-Rad Microplate Reader (Hercules, Calif.) with a 96-well format. Two hundred microliter aliquots of an elastase solution (0.2 units) were assayed per well, and 20 microliters of a 60 micromolar substrate solution was added to initiate the enzyme reaction.

Inhibition of Elastase Activity with Dialdehyde Starch

Elastase activity was measured in dialdehyde starch solutions. Solutions of dialdehyde starch (Sigma) were prepared in the buffer described above at concentrations of 100 to 0.1 micromolar. The dialdehyde starch solutions were incubated with stirring in Reacti-Vials with 0.2 units/mL of elastase for an hour. The solutions were centrifuged at 1200×g for five minutes and the supernatant was assayed for elastase activity as described above.

Results

Cotton gauze was subjected to phosphorylation, oxidation, and sulfonation. The degree of substitution (D.S.) was determined by a standard degree of substitution relationship for cellulose (based on the percent of total phosphorous and sulfur for the phosphorylated and sulfonated samples). Base titration of free carboxyls was employed to determine D.S. levels on carboxymethylated cotton cellulose (CMC). The phosphorylated and sulfonated cotton cellulose D.S. levels were 0.035 and 0.011 respectively. This corresponds to one phosphate for every 28 anhydroglucose units and one sulfate for every 91 anhydroglucose units. The degree of substitution for the dialdehyde was also 0.011 since the bisulfite addition reaction is utilized to determine D.S. levels for dialdehyde cotton. The degree of substitution for CMC was 1.4.

Effect of Modified Gauzes on Elastase Activity

Initial experiments examined the ability of the modified cotton celluloses to absorb purified neutrophil elastase. Twenty-five, fifty and seventy-five milligram quantities of gauze were soaked to saturation for an hour in one milliliter of buffered solution containing 0.2 units of elastase. Unbound enzyme was removed by filtration followed by pressing under high pressure. The recovery of buffer from the filtration process was found to be 90%.

Figure 2A:
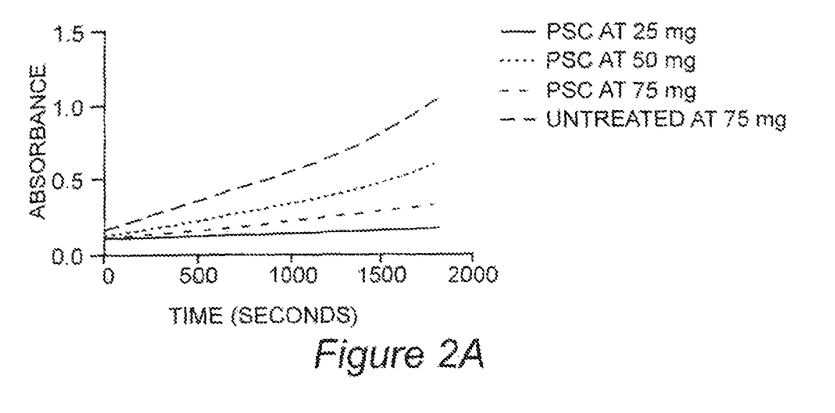
FIGS. 2A-C. Reaction progress curves for gauze-treated solutions of elastase. Substrate hydrolysis was performed with a 60 mu.M solution of MeOSuc-Ala-Ala-Pro-Val-pNA and reaction rates monitored by spectrophotometric measurement of the release of p-nitroaniline at 405 nm. 25, 50 and 75 mg samples of phosphorylated cotton gauze (PSC, 5A), sulfonated cotton gauze (SOC, 5B) and dialdehyde cotton gauze (DAG, 5C) were compared with 75 mg of untreated cotton gauze (UT).
Figure 2B:
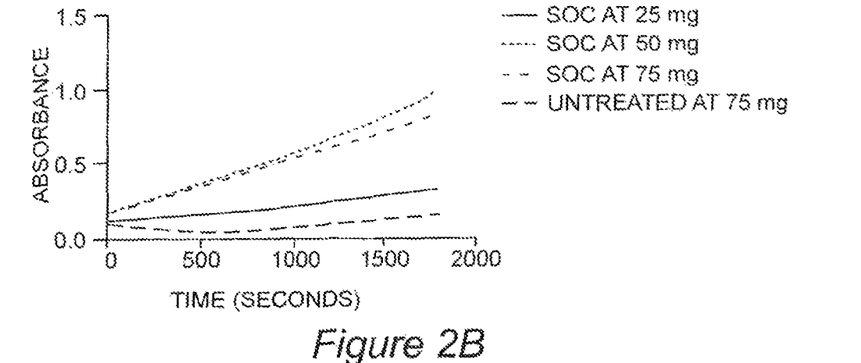
Figure 2C:
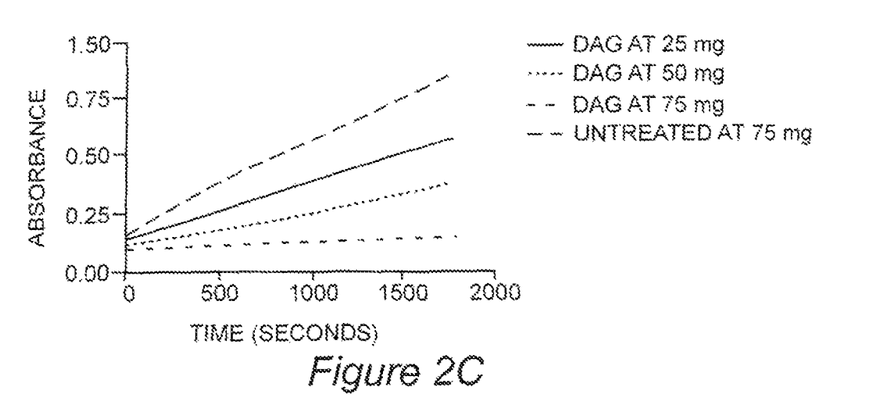
Figure 3:
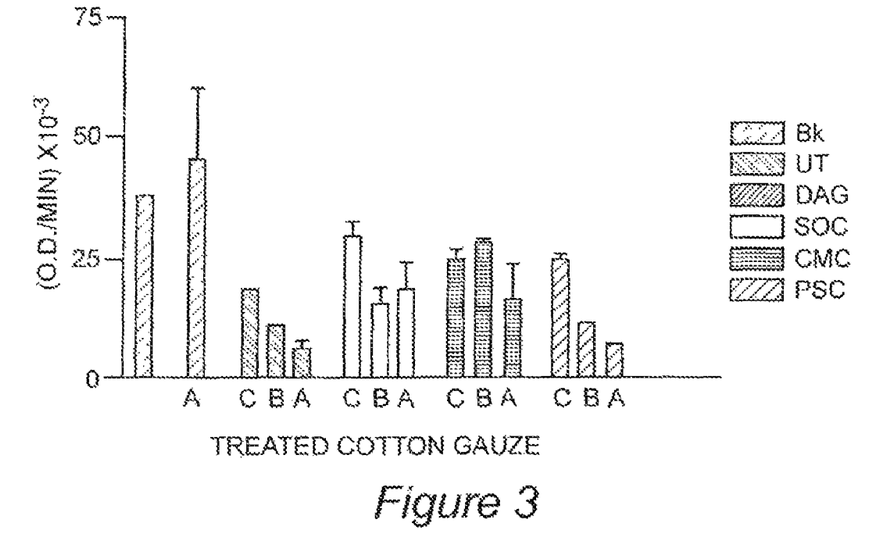
FIG. 3 Initial velocities ($v_o$) of residual elastase activity in samples exposed to untreated gauze (UT), dialdehyde gauze (DAG), sulfonated gauze (SOC), carboxymethylated gauze (CMC) and phosphorylated gauze (PSC), compared to a sample that was not treated with gauze (Bk). Weights of gauze samples were 75 (A), 50 (B), and 25 {circle over (C)} mg. Data are mean±S.D. of triplicate determinations. All are significantly different from control, $p<0.05$, as determined by analysis of variance.

The assessment of elastase activity in solution exposed to the treated gauze was performed on the unbound enzyme. Acid-extractable elastase activity was assayed in a 96-well format using MeOSuc-Ala-Ala-Pro-Val-pNa for substrate hydrolysis. The kinetics of elastase activity is based on the relative initial velocity ($v_o$) values for enzyme solutions exposed to cotton gauze. In this study 0.2 units of elastase were tested per sample. Measurement of elastase activity remaining in solution upon treatment with the gauze was accomplished by monitoring the reaction rate within a thirty-minute time frame. The reaction progress curves for the treated samples are shown in FIG. 2a-c. A decrease in active enzyme sites is apparent from the decreasing dose response relation of the treated gauze samples with dialdehyde, sulfonated, and phosphorylated cotton. The decreased rate reflects a decrease in units of elastase activity retained in the eluted buffer. A plot of $v_o$ values shown in FIG. 3 for the samples also demonstrates this dose response relationship. The plot of $v_o$ values was within the same range for the dialdehyde, sulfonated and phosphorylated cotton. A similar decrease in velocity was demonstrated with increasing weight of treated gauze.

The lower $v_o$ values for the treated samples when compared with the untreated cotton gauze suggests that the elastase activity is retained in the treated cotton gauze due to selected modifications on the gauze. Retention of elastase activity in treated gauze was found to be four-fold higher than in untreated gauze.

To assess whether the dialdehyde cotton gauze may act through active site uptake of elastase, dialdehyde starch was employed as a soluble aldehydic polysaccharide that may bind elastase. The results demonstrated that inhibition of elastase by dialdehyde starch is observed within a low micromole range, which is an inhibitory concentration within the titer of aldehydes per gram of dialdehyde cotton used in the current study. Thus, inhibition of elastase activity by a soluble form of a high molecular weight aldehydic carbohydrate suggests that the dialdehyde cotton gauze may function as a serine protease sequestrant through active site access to elastase.

Non-specific binding of the enzyme by the dialdehyde cotton gauze is an alternative explanation for elastase inhibition by dialdehyde cotton gauze. Since aldehydes can form Schiff bases with protein amino groups the potential for Schiff base formation between the protein amino groups of elastase and the aldehydes of dialdehyde cotton (DAG) was a concern. To mimic the effect of protein amines a high molecular weight polylysine was employed. Polylysine is a single amino acid biopolymer containing only epsilon amines as the side chains of the primary amino acid structure. To test for a potential non-specific Schiff base reaction effect between the elastase and the DAG, the dialdehyde cotton was incubated in a polylysine solution and elastase added to the solution to test for retention of elastase-lowering activity. DAG retained its inhibitory effect on elastase in the presence of polylysine. Based on this result it may be inferred that proteinaceous amines do not interfere with the observed elastase-lowering effects of the dialdehyde cotton gauze.

Elastase-Lowering Activity in Wound Fluid

The dialdehyde cotton gauze (DAG) was selected for further evaluation using human wound fluid. To assess the ability of the modified gauze to lower wound fluid-containing elastase activity in comparison to untreated gauze (UT), DAG samples and UT were placed in wound fluid in a range of 2.5 to 20 milligrams of gauze per microliter of patient wound fluid. After exposure to the DAG or UT, the solutions of chronic wound fluid were assessed for residual elastase activity using a known elastase substrate The results showed that the chronic wound fluid which had been exposed to DAG possessed less elastase activity than that which had been exposed to UT at each quantity of gauze tested. This suggests that more elastase has been sequestered by DAG than by UT. Increasing the quantity of DAG resulted in a dose dependent decrease in the amount of retained elastase activity.

These results reflect the superior ability of the DAG samples to remove elastase activity from wound fluid as compared to untreated cotton gauze. Dialdehyde cotton gauze extracted 2-5 fold more elastase activity with increased gauze loading per volume of wound fluid when compared with untreated gauze.

Measurement of protein levels remaining in the wound fluid following incubation with the gauzes was performed to compare the relative amounts of protein taken up by treated and untreated gauze. Lower levels of protein were found in the wound fluid soaked with DAG than with the untreated cotton. This is consistent with the lower activity of elastase found in the wound fluid soaked with DAG samples.

The results obtained demonstrate that dialdehyde cotton effects the sequestration of the protease elastase from wound fluid.

Figure 4A:
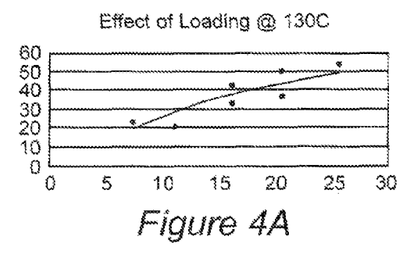
FIG. 4a-f are graphs of optimization experiments show the amount of reagent used for phosphorylation of the substrate versus the sequestering properties of the products at three different temperatures (4a-c), and for the silver derivative of the equivalent phosphorylated substrate at the same temperatures (4d-f).
Figure 4B:
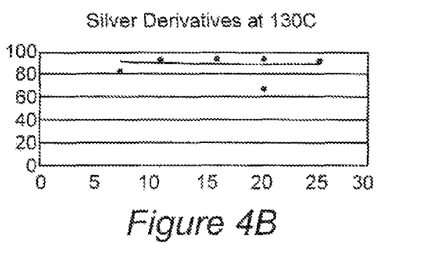
Figure 4C:
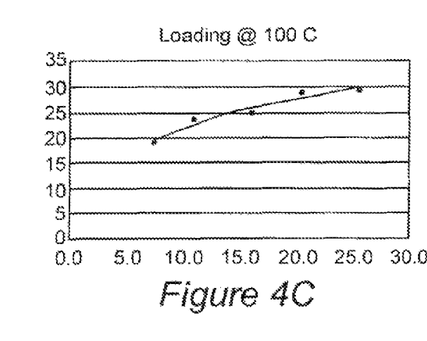
Figure 4D:
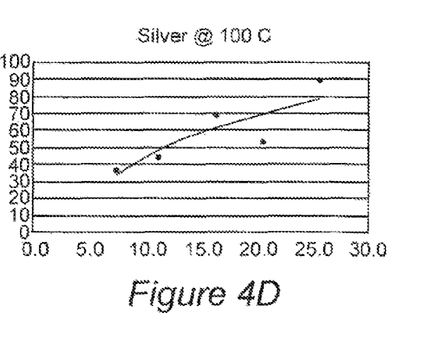
Figure 4E:
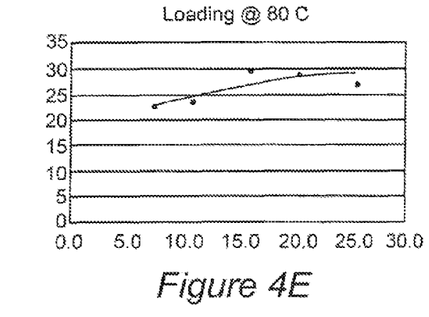
Figure 4F:
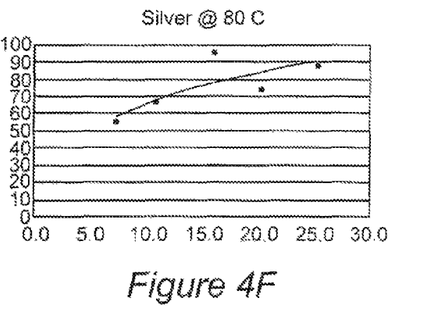

We have optimized phosphorylation of cellulosic materials to achieve products with exceptional sequestering properties for elastase and other proteases. These optimization involved utilization various phosphorylation reagents, achieving products with great sequestering properties at high product throughput and lower reagent utilization. FIGS. 4a-d for example show phosphorylation of cotton gauze with monoammonium phosphate (MAP) in the presence of urea (U) at different loading at mild temperatures. In these figures the X-axis represent the % solid content of fabric before curing (MAP+U) and the Y-axis is the % elastase sequestration (using pure neutrophil elastase at 20 mu/ml and fabric to liquid ratio of 50 mg/1 ml soln). All the fabrics had been cured for 6 minutes. It is interesting to note that (FIGS. 4A, B, C) we can carry out these reactions at temperature as low as 130 C to achieve products with good elastase sequestering performance (Elastase Sequestering for cotton is about 25% using pure elastase). But it is more interesting to note that silver derivatives of these phosphorylated cotton gauzes have outstanding elastase sequestering properties (see, FIGS. 4C and D) whereas silver derivative of product formed at 80 C does not show this performance. Silver derivatization was achieved by bringing 1 g of phosphorylated product with 10 ml of silver nitrate solution (200 ppm silver nitrate) for about 2 minutes followed by rinsing with excess deionized (DI) water. No free silver nitrate remains on the fabric which is white. It is apparent that phosphorylation at 80 C is not adequate enough to make good performing silver derivative (FIG. 4E). Additional benefits of these transition metal derivatives, such as silver or copper, is that in addition to their great elastase sequestering performance they also possess antimicrobial properties.

Moreover, by incorporating alginates and starches into cellulosic products we have made products with high liquid sorption and liquid retention capabilities. In experiments described below we used ammonium alginate, Protamon S obtained from FMC Biopolymer, Philadelphia Pa. Other types of alginates such as sodium alginate, potassium alginate, magnesium alginate or alginic acid could be used as well in the wound dressing applications contemplated by this invention. Alginates are biopolymers of mannuronic (M) and glucoronic (G) acids. Alginate occurs in the seaweed as a mix of calcium, magnesium, sodium and potassium salts. The process of manufacturing of this product from the seaweed involves extraction of the alginic acid from the weed followed by neutralization by different salts to prepare appropriate product. Depending on the source of the seaweed and the extraction process different grades of product with different M and G ratio and sequence and molecular weight are obtained. Depending on the molecular weight of the alginate, different viscosity is obtained at the same concentration. Above 2.5% wt/wt solution the ammonium alginate we used produced solutions with viscosity over 200 centipoise at room temperature so we kept concentration below this value.

Elastase Sequestering Performance:

The elastase sequestering performance of our products was measured by placing 50 mg of the product in 1.00 ml of Simulated Wound Fluid (SMFL). SMFL was prepared by dissolving leukocyte elastase into buffer at concentration of 20 m. unit/ml. Included in SMFL is 0.1% bovine serum albumin (BSA) to simulate average chronic wound. We have found that this formulation has activity similar to "average" chronic wound and allows us to compare performance of different wound care product to each other and to controls. The elastase sequestering performance of the product is obtained by comparing the activity of the SMFL fluid before and after equilibration (2 hr) of the fluid with the product.

Competitive Liquid Sorption and Retention

This procedure is to simulate the performance of products according to the invention when they are in touch with another liquid absorber. These absorptive materials retain fluid better than the standard cotton dressing. Therefore there is not only absorption of fluid, but he absorb fluid is retained within the dressing. Clinically this means that dressing could be left in the wound for longer period of time and the normal skin adjacent to the wound would be less likely to be macerated. This procedure is to simulate fluid sorption capacity of wound care products according to the invention as compared to average liquid sorption capacity of cotton gauze or paper towel. The experiment is carried out in the following manner. A piece of the product (0.1 to 1.00 gram) is allowed to come in contact with water for 60 seconds. The amount of the water used in this experiment is in excess of total sorption capacity of the product and we keep it to 1.5 ml water per 0.1 g of the product. So if the wound care product is 0.2 gram, we use 3.0 ml and if 0.5 gram, we use 7.5 ml of water.

After the product has soaked the water, it is removed and placed flat on 10 folds of dry paper towels allowing excess water to drain away for 90 seconds. The product is then weighed accurately and the % water retained under this competitive condition is calculated as described below;

% Competitive Water Sorption/Retentive=100×($Wt_{90\,sec}$−$Wt_{Original}$)/$Wt_{Original}$ Where $Wt_{90\,sec}$ is the weight of the dressing after 90 second of contact with the dry paper towel and $Wt_{Original}$ is the original weight of the dressing. This property will be referred to % water retention throughout this patent (% WRC).

Alginate and Silver Alginate Solution Preparation
Preparation of 2.2% Alginate Solution:
Dissolved 10.0 gram of ammonium alginate in 449.0 grams of water and mixed overnight to achieve uniform solution. Solutions above 3% had too high viscosity and were difficult to handle without heating.

Preparation of 1.1 wt ° A, Alginate 10% Neutralized with Silver Nitrate

Alginate solution was diluted by mixing 40 gram of the 2.2% alginate solution with 30 gram of DI water. Silver nitrate (Reagent Grade) from Baker was dissolved in DI water (77.4 mg in 5 ml) and added drop wise into the alginate solution with rapid agitation. A semi-clear solution resulted after overnight agitation. This "solution" will settle if left standing indicating gel formation. When we attempted to make higher concentration solutions, insoluble gels were formed which were hard to handle. Also when we attempted making silver alginate solutions above 10% neutralization (molar), gel formation made this product difficult to handle. Therefore a major drawback of making silver alginate and using them for making products is difficulty of handling gels. Despite this difficulty, in some applications, silver alginates may be preferred.

Highly liquid retentive dressings can be formed by coating of cotton or phosphorylate cotton with alginate and silver alginates as shown in Table 1.

TABLE 1

| Examples | Description | % Elastase Seq. SWFL | % CWR |
|---|---|---|---|
| Comparative 1 | Cotton Gauze | 16.0 | 100 |
| Comparative 2 | PhosCot | 44.2 | 100 |
| Example 1 | PhosCot w/3.7% Alg | 45.3 | 513 |
| Example 2 | PhosCot w/3.7% Silver Alg (10%) | 77.7 | 540 |
| Comparative 3 | Cotton w/3.7% Alg | 26.3 | 583 |
| Example 3 | Cotton w/3.7% Alg (10% Silv) | 79.4 | 436 |

In Table 1, PhosCot stands for phosphorylated cotton. Comparative Example 1 shows the behavior of common cotton which has low elastase sequestering performance and also low competitive liquid retention capacity. PhosCot (Comparative Example 2) has significantly higher elastase sequestering property, but it has low % CWR. Cotton coated with alginate (Competitive Example 3) has high % CWR, but it has low % elastase sequestering properties. On the other hand when phosphorylated cotton is coated with alginate (Example 1) or with silver alginate (Example 2) we have products with both good % Elastase sequestrations and % CWR. We can also achieve good performance when coating cotton with silver alginate (Example 3). As we have mentioned in the silver alginate solution preparation the viscosity and gel formation is a difficulty that could be avoided by other approaches of preparing these products by different processes as described below.

Desirable products (Table 2) were prepared by coating cotton (Example 4) or phosphorylated cotton (Example 5) with ammonium alginate in the first step, and then exposing the alginate coated fabric to silver nitrate solution to convert alginate into silver alginate to get product with high elastase sequestering properties (% CWR was not measured for these samples but were high). We used 1000 ppm silver nitrate solution for this derivatization. The advantage of this process is that one does not have to deal with gels of silver alginate, but the disadvantage of this process is that during the silver conversion a portion of the alginate is transferred into the silver nitrate solution (in form of gels) and from stand point of process control this type of product formation is not as desirable as process described below.

TABLE 2

| Fabric Process | | % Elastase Sequestering (SWFL) |
|---|---|---|
| Example 4 | Cotton W/4% Alginate Then Silver Nitrate | 61.2 |
| Example 5 | Phosphorylated cotton with 4% Alginate, then Silver Nitrate | 59.4 |

In this more preferred embodiment, the phosphorylated cotton gauze (Comparative 2) is reacted with soluble silver compounds such as silver nitrate or acetate to form silver complex with exceptional elastase sequestering capacity (Comparative 4). However the % CWR capacity of this product is not much different than that of cotton. When such a product is then coated with alginates, products with exceptional elastase sequestering and % CWR are obtained (Examples 6 and 7).

TABLE 3

| Examples | Description | % Elastase Seq. (SWFL) | % CWR |
|---|---|---|---|
| Comparative 2 | PhosCot | 44.2 | 100 |
| Comparative 4 | PhosCot, Silver derivative (1000 ppm AgNO3) | 85.0 | 100 |
| Example 6 | PhosCot, Silver derivative (1000 ppm AgNO3), then 4% Alginate | 79.0 | 275 |
| Example 7 | PhosCot, Silver derivative (1000 ppm AgNO3), 6% Alginate | 72.5 | 383 |

While phosphorylated cotton is preferred in the present invention, other polysaccharide derivatives may complex with silver such as phosphorylated starch, carboxymethyl cellulose, dialdehyde gauze, and sulfonated gauze, and those of skill in the art will recognize that the invention can be practiced with polysaccharides which have the capacity to form complexes with transition metals such as silver or copper.

It is also understood by those of skill in the art that these alginate containing products could be cross-linked by exposure to multivalent cations such as $Ca^{2+}$, $Cu^{2+}$, or $Al^{3+}$ without affecting their elastase sequestering properties or their % CWR capacities as shown by examples that follow. In these examples, after coating the fabric with alginate or silver alginate, the products were brought in contact with 200 ppm calcium chloride (Ca) or copper sulfate (Cu) and then the performances were measured. As seen these products have great performances. Additionally these products having large supply of silver or copper will have antibacterial and antifungal properties.

TABLE 4

| Examples | Description | % Elastase Seq. (SWFL) | % CWR |
|---|---|---|---|
| Example 8 | PhosCot w/3.7% Alg, then Ca | 50.1 | 363 |
| Example 9 | PhosCot w/3.7% Alg (10% Silv), then Ca | 56.2 | 453 |
| Example 10 | PhosCot w/3.7% Alg, then Cu | 53.1 | 364 |
| Example 11 | PhosCot w/3.7% Alg (10% Silv), then Cu | 67.1 | 385 |

These products have exceptional performance as dressings for chronic wounds where management of exudates fluids is critical in treatment of this class of wounds.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A wound dressing consisting of:
   a silver-derivitized phosphorylated cotton support matrix wherein silver is bound chemically to the support matrix; and
   a silver alginate coating.
2. The wound dressing of claim 1, which is white.

* * * * *